United States Patent [19]

Dussault

[11] 4,414,197

[45] Nov. 8, 1983

[54] METHOD FOR PREPARING PERMANENT SLIDES OF RARE SORTED CELLS

[75] Inventor: Richard A. Dussault, Seekonk, Mass.

[73] Assignee: Ortho Diagnostic Systems Inc., Raritan, N.J.

[21] Appl. No.: 360,119

[22] Filed: Mar. 19, 1982

[51] Int. Cl.$^3$ ............................................. G02B 21/34
[52] U.S. Cl. ...................................... 424/3; 350/536; 422/61; 427/2; 436/177
[58] Field of Search ............... 436/513, 807, 808, 174, 436/177; 427/2; 424/3; 350/534, 536; 422/61

[56] References Cited

U.S. PATENT DOCUMENTS

| | | | |
|---|---|---|---|
| 2,090,914 | 8/1937 | Porter | 350/536 |
| 3,495,926 | 2/1970 | Naz | 424/3 X |
| 3,768,914 | 10/1973 | Kinney et al. | 350/536 X |
| 3,904,781 | 9/1975 | Henry | 424/3 X |
| 3,960,489 | 6/1976 | Giaever | 436/807 X |
| 4,172,827 | 10/1979 | Giaever | 435/7 X |

OTHER PUBLICATIONS

Shandon Southern Instruments Inc. Pathology Equipment Catalog, pp. 2-3.
Schumann, G. B. et al., An Improved Technique for the Evaluation of Urine Sediment, Laboratory Management, Oct. 1977.
Garnet, Jr.; R. F. et al., Rapid Screening for Lupus Erythematosus Cells Using Cytocentrifuge-prepared Buffy Coat Monolayers, American Journal of Clinical Pathology, vol. 67, No. 6, Jun. 1977, pp. 537-539.
Hansen, H. H. et al., The Cytocentrifuge and Cerebrospinal Fluid Cytology, Acta Cytologica, vol. 18, No. 3, 1974, pp. 259-262.
Flanagan, M. J. et al., Evaluation of Bladder Washing Cytology For Bladder Cancer Surveillance, The Journal of Urology, vol. 119, pp. 42-43, 1978.

*Primary Examiner*—Arnold Turk
*Attorney, Agent, or Firm*—Mark A. Hofer

[57] ABSTRACT

Methods and apparatus wherein a very small number of sorted cells are attached to specified locations on a microscope slide circumscribed by well areas of a retainer slip. The cells are deposited in the wells and during centrifugation of the slide-retainer sandwich, are contacted with and attached to the serum albumin present in the well and coated on the slide. Removal of excess fluids, optional clamping means and the retainer slip followed by air drying provides for permanent attachment of rare, sorted cells in a localized, known area for subsequent staining, examination and analysis.

4 Claims, 4 Drawing Figures

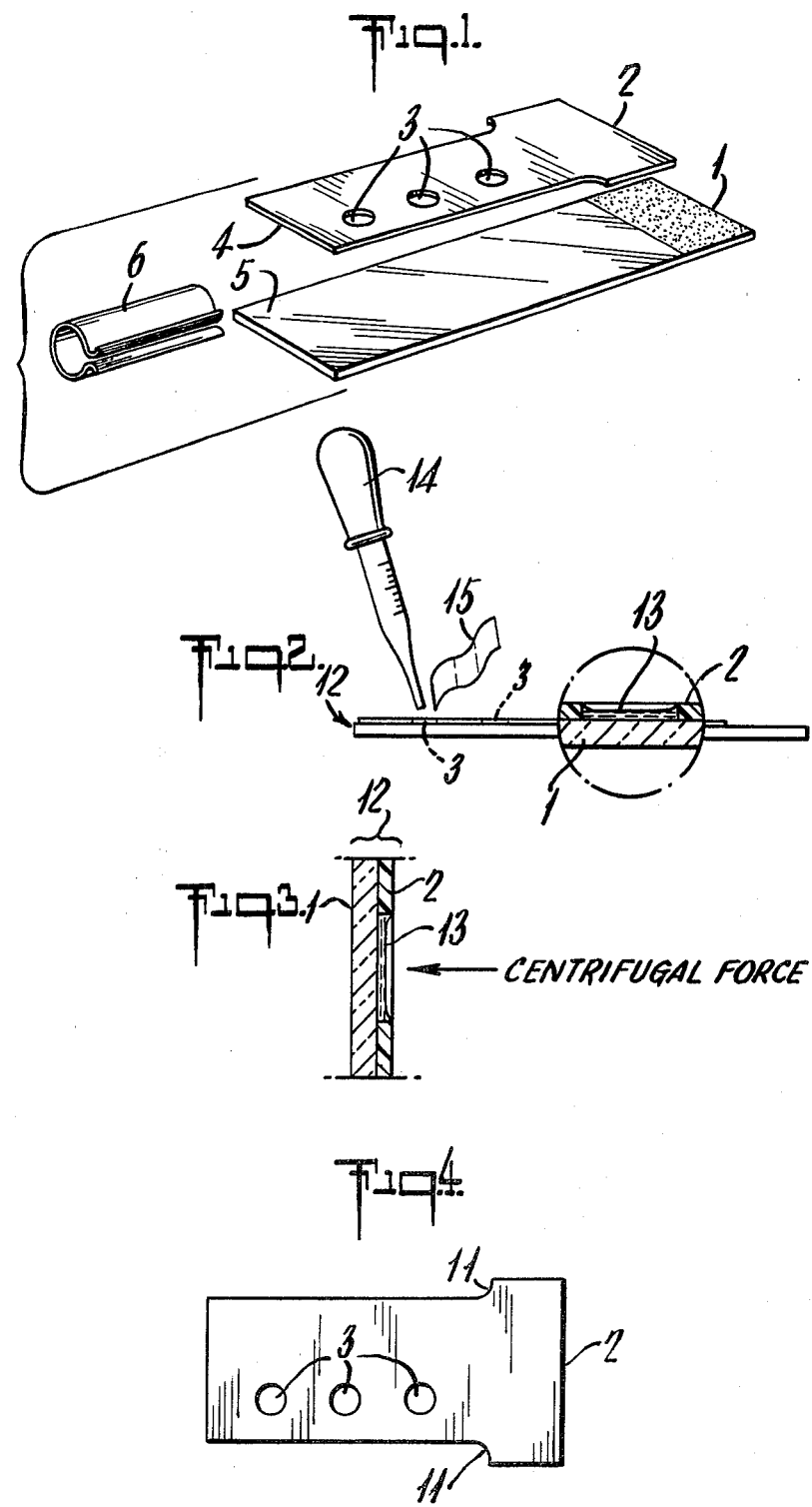

METHOD FOR PREPARING PERMANENT SLIDES OF RARE SORTED CELLS

FIELD OF THE INVENTION

This invention relates to a method for preparing permanent slides of cells sorted by electrostatic cell sorters or bulk gradient separation processes.

BACKGROUND OF THE INVENTION

Flow cytometry is a relatively new and rapidly changing technology and has evolved into a sophisticated analytic tool for rapidly quantitating multiple chemical and physical properties of individual cells or cellular constituents of heterogeneous populations. The value of flow cytometry in biological research can be seen in its ability to reveal information concerning the cell cycle kinetics, DNA ploidy levels, and the quantitation of cell surface antibodies. The sophisticated technical achievements made possible by this instrumentation find clinical applications in cancer cell detection, blood cell counting, performing differential white blood cell counts, drug effectiveness studies including cancer chemotherapy, monitoring leukemia in other solid tumors, as well as uses in immunology and virology. Additional biologic applications are continuously being discovered even as the flow cytometry techniques continue to undergo dramatic improvements.

Typically, cell sorting is accomplished by instruments generally measuring a multitude of parameters. Most conventional cell cytometers employ some type of hydrodynamic focusing whereby the cells to be measured are aligned in a single file fashion within a fluid sheath. The cells are then passed by a detector region which measure either a change in electrical properties of a small aperture as the cell passes therethrough or the light scattering effects occasioned by the passage of the cell past a light source. Since different cells typically exhibit varying characteristics, detection of the dynamic effects occasioned by the passage of the cell provides data useful in discriminating and quantitating between cell populations. With the addition of cell sorting capabilities, such an instrument can analyze a mixed population of cells, discriminate between cell types and physically manipulate the cells, generally by employing electrostatic principles or variations thereof, so that they may be concentrated to greater purity. This is generally accomplished by the deposition of the cells into vials or similar type of containers.

In order to monitor the type of cells collected in this fashion and to appropriately adjust the window parameters for the effective discrimination for and collection of desired cell types, the cells must be examined microscopically. With large numbers of cells, this may be accomplished by the deposition of the cells onto a microscope slide, and after staining procedures, easily found because of their pervasive presence on the slide. Great difficulty is encountered, however, when the population of selected cells is very small, i.e. on the order of a hundred cells. Indiscriminate application of such a small number of cells to a microscope slide will force the microscopist on a hunt and search detail in order to assure that he has correctly identified representative cell types in that small population.

In order to reduce this difficult and demanding task, conventional methods have dictated the use of microscope slides having concave areas for the deposition of cells in one spot. This method has been effectively employed in tissue culture and tissue typing since the accumulation of cells in a localized spot has aided in the detection of seralogical reactions. For examination of single cells, this method is not desirable since all the cells are coalesced in a very localized area and consequently, often physically overlap one another. Further, such a system is primarily useful for cells in suspension and does not allow the facile employment of typical staining methods such as Wright stain and the like.

It is an object of the present invention to provide an apparatus capable of permitting the examination of a small number of cells that have been sorted by a cell sorter and to provide their attachment to a microscope slide in a manner consistent with standard staining techniques.

Another conventional method employs a cup for the collection and retention of cells in conjunction with the use of a centrifuge. This system has also proven to be ineffective since the cups are designed to contain a large volume and the desired rare cells are typically in very small numbers. With such a high dilution, it consequently becomes extraordinarily difficult to locate the cells for subsequent staining and examination.

It is an object of the present invention to provide apparatus and methodology whereby rare sorted cells may be permanently attached onto a slide for subsequent staining and examination and that despite the small number of cells, their fixation, staining, and localization in a specified limited site provides for reduced probability of loss and destruction as well as increased handling ease.

SUMMARY OF THE INVENTION

In accordance with the principles and objectives of the invention, there is provided a system for collecting and preparing permanent slides of rare sorted cells comprising means for retaining, in specified locations, sorted cells having wells and adapted for contacting a microscope slide to form a slide-retainer sandwich. Prior to forming the slide-retainer sandwich, the sides of the microscope slide and retainer means are coated with serum albumin which aids in the elimination of capillary seepage and retention of the cells. An additional amount of serum albumin is added to the wells and the sorted cells are then added thereto. Centrifugation of the slide-retainer sandwich results in the attachment of the cells to the microscope slide via the serum albumin. Thereafter, the retainer means and excess fluids are removed and the cells, attached to the slide in known, localized areas, are ready for subsequent staining.

BRIEF DESCRIPTION OF THE DRAWINGS

The objectives of the invention and the preferred embodiments thereof will best be understood by reference to the accompanying drawings wherein:

FIG. 1 is a perspective view of the preferred embodiment;

FIG. 2 is a cross-sectional view of a well in the retainer-slide sandwich;

FIG. 3 is a cross-sectional view of FIG. 2 showing its orientation with regard to the application of centrifugal force; and FIG. 4 is a top view of the preferred embodiment of the retainer cover slip.

BEST MODE FOR CARRYING OUT THE INVENTION

FIG. 1 illustrates the manner in which the device of the present invention is to be employed. A standard microscope slide 1 is cleaned using ethanol or alcohol wipes preferably containing approximately seventy percent isopropyl alcohol. Although the slide shown has a frosted area intended for labeling purposes, such an area is an optional feature to be selected at the whim of the user and is not required for the operation of the invention. The cell retaining cover slip or retaining means 2 is preferably dimensioned for contact with the working area of the microscope slide 1. The retainer 2 will have at least one well 3 but, preferably will have a plurality of wells in order to allow for multiple sample analysis. The diameter, spacing and number of wells 3 will be adjusted in accordance with sample volumes and cell numbers contained therein and user preference. Well diameters of 0.170 inches and spacing between centers of ½ an inch have been found effective.

Prior to contacting the retainer cover slip 2 to slide 1, surfaces 4 and 5 of the retainer slip and slide respectively are coated with an effective layer of serum albumin. the serium albumin is preferably bovine serum albumin in a relatively low concentration such as 2–5% in phosphate buffered saline. The diluted bovine serum albumin solution will preferably contain sodium azide at a concentration in the neighborhood of 0.01% as a bacteriostat. Application of the bovine serum albumin can be effectively accomplished by smearing one surface with the edge of another microscope slide similar to the technique typically employed in making blood sample smears.

The retainer slip 2 is then contacted with the slide 1 to form a sandwich 12 as shown in FIG. 2. In order to assist in maintaining the integrity of the sandwich, it is preferred that a retaining clamp 6 is added. If a clamp is employed such a feature although preferred, is optional; the wells 3 on retainer clip 2 are advantageously located appropriately in order to avoid conflicting contact.

With reference to FIG. 2, additional serum albumin is added to well 3 to form a built up layer 13 contained by the well. Preferably, the same concentration and type of serum albumin is employed and a sufficient volume is used to fill the well approximately ⅓–½ full. Using a retaining cover slip having a thickness of 0.060 inches and a well having a diameter of 0.170 inches, it has been found that an effective volume is approximately 6 microliters. Thereafter, the cells are sorted either directly into the well from the cell sorter apparatus or are added via micropipette 14 or other means. It is preferable that the total volume added to the well 3 be limited to approximately 8 microliters in order to avoid spillage and loss of cells. The slide-retainer sandwich with the cells is then placed in a Cytocentrifuge ™ produced by Shandon or its equivalent. The well opening faces the center of the rotor carousel so that the centrifugal force is applied to the sandwich 12 as shown in FIG. 3. The sandwich is then centrifuged at approximately 600 rpm for about 4 minutes so that the cells are contacted with and retained by the serum albumin. The figures for rotational speed and time of centrifuging may be adjusted as necessary in order to effect firm attachment of the cells and avoid morphological damage.

The excess supenatant from the original cell suspension is then preferably removed at this time by siphoning off the fluid using filter paper, micropipette or porous plastic means as illustrated by the tissue representation 15 in FIG. 2. Separate siphoning means are preferably employed for each well in order to prevent contamination. Proper removal of the supernatant reduces the possibility of cell membrane destruction upon evaporation of surrounding saline.

At this point, the cell retaining slip 2 is removed from the slide 1 in a manner avoiding disturbance of the cell areas. Preferably this is done by grasping the microscope slide 1 at the frosted area and holding the sandwich at a slight angle. The retainer cover slip is then slowly and gently removed by lifting the small protruding handles 11 shown in FIG. 4. It is preferred that as this physical operation is accomplished, a line of serum albumin solution should be seen to recede towards the end of the slide without passing through the area where the cells are secured. Remaining excess serum albumin may be removed with a piece of tissue or lense paper, again avoiding those areas where the cells have been attached. The slide and the attached cells are then allowed to dry preferably by simple evaporation. The cells may then be conveniently stained as desired.

What is claimed is:

1. A method for preparing permanent slides of rare sorted cells present in a suspending solution comprising the steps o:
   (a) providing a microscope slide;
   (b) further providing means for retaining cells, said retainer means having at least one well;
   (c) coating one side of both the microscope slide and the retainer means with an effective amount of serum albumin for substantially sealing capillary passages between the slide and retainer means;
   (d) contacting together the coated sides of the microscope slide and retainer means to form a slide-retainer means sandwich;
   (e) partially filling the well with an effective amount of serum albumin for retaining the cells in the well;
   (f) depositing the sorted cells into the well;
   (g) centrifuging the slide-retainer means sandwich whereby the cells are contacted with and retained by the serum albumin; and
   (h) removing the retainer means and excess suspending solution.

2. The method as described in claim 1 wherein the contacting step further comprises: holding the slide and retainer means together with means for clamping, and the removing step further includes removing the means for clamping.

3. The method as described in claim 2 wherein removing excess suspending solution comprises: siphoning excess suspending solution by capillary action and drying the microscope slide.

4. The method as described in claim 1 or 3 wherein the serum albumin is bovine serum albumin.

* * * * *